United States Patent [19]

Bianco

[11] Patent Number: 5,258,374
[45] Date of Patent: Nov. 2, 1993

[54] METHOD OF TREATMENT OF ALLERGIC CONJUCTIVITIS

[75] Inventor: Sebastiano Bianco, Milan, Italy

[73] Assignee: Hoechst Aktiengesellschaft, Frankfurt am Main, Fed. Rep. of Germany

[21] Appl. No.: 731,993

[22] Filed: Jul. 18, 1991

[30] Foreign Application Priority Data

Jul. 20, 1990 [DE] Fed. Rep. of Germany ....... 4023086

[51] Int. Cl.$^5$ ........................................... A61K 31/635
[52] U.S. Cl. ................................... 514/158; 514/912
[58] Field of Search .............................. 514/158, 912

[56] References Cited

U.S. PATENT DOCUMENTS 4,908,382  3/1990  Bianco ................................ 514/471

FOREIGN PATENT DOCUMENTS 0386700   9/1990  European Pat. Off. .
WO90/09792 9/1990  PCT Int'l Appl. .

OTHER PUBLICATIONS

M. Robuschi, MD, M. Pieroni, MD, M. Refini, MD, S. Bianco, MD, G. Rossoni, PhD., F. Magni, PhD., and F. Berti, PhD, "Prevention of Antigen Induced Early Obstructive Reaction by Inhaled Furosemide in (atopic) Subjects with Asthma and (actively sensitized) Guinea Pigs", J. Allergy Immunol. 85(1):10–16 (1990).

S. Bianco, et al., "Prevention of Exercise-Induced Bronchoconstriction by Inhaled Frusemide," The Lancet, vol. II:252–255 (Jul. 30, 1988).

S. Bonini, et al., "Conjunctival Provocation Test as a Model for the Study of Allergy and Inflammation in Humans," *Int. Arch. Allergy Appl. Immunol.*, 88:144–148 (1989).

C. Moller, et al., "The Precision of the Conjunctival Provocation Test," Allergy, 39:37–41 (1984).

S. Bonini, et al., "Inflammatory Changes in Conjunctival Scrapings After Allergen Provocation in Humans," *J. Allergy Clin. Immunol.*, 82:462–469 (1988).

*Primary Examiner*—Zohreh A. Fay
*Attorney, Agent, or Firm*—Finnegan, Henderson, Farabow, Garrett & Dunner

[57] ABSTRACT

Furosemide

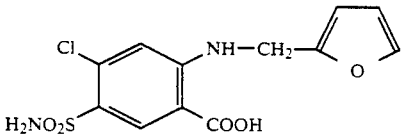

is used as medicament for the treatment of allergic conjunctivitis; it is dropped into the conjunctival fornix of the eye.

1 Claim, 13 Drawing Sheets

METHOD OF TREATMENT OF ALLERGIC CONJUCTIVITIS

The invention relates to a method of treating allergic conjunctivitis.

Furosemide is a well known diuretic

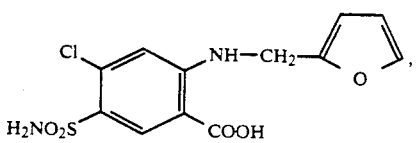

moreover furosemide is known as a medicament for preventing of or treating of asthma (cf. The Lancet, Jul. 30, 1988, p. 252).

Now we have found that furosemide is a valuable medicament for treating of allergic conjunctivitis, which was neither anticipated nor suggested by the state of the art. The invention relates also to a method of treating or preventing allergic conjunctivitis consisting in administering an appropriate amount of furosemide to the conjunctival fornix of the eye, as well as to the use of furosemide for this purpose; and to the use of furosemide for the production of a medicament for treating or preventing allergic conjunctivitis.

MATERIALS AND METHODS
PATIENTS 10 subjects with a clinical history of seasonal allergic conjunctivitis with or without rhinitis or asthma, and with a positive skin test to grass pollen were studied. Clinical characteristics of the patients are reported in table I. All the subjects were untreated, and the experiments were entirely conducted outside the pollen season.

METHODS

The allergic conjunctival test was performed as described by Bonini S, Bonini S, Berruto A, Tomassini M, Carlesimo S, Bucci MG, Balsano F. Conjunctival provocation test as a model for the studiy of allergy and inflammation in humans. Int Arch Allergy Appll Immunol 1989, 88:144–148.

Briefly, in a preliminary day, an end-point titration of skin sensitivity was performed using increasing dilutions (dilution factor 3.2) of the allergen in physiological saline containing 0.03% human serum albumin (range 10.000 to 3 RAST Units $ml^{-1}$, Frazioni alfa, Bayropharm Italians, Milan, Italy) on the forearm. The lowest dose giving after 15 to 20 minutes a weal and flare reaction with a diameter greater of at least 2 mm compared to the negative control, was then used as the first dose for the allergen conjunctival test.

For the conjunctival challenge, the patient was placed with the head reclining upside, and a drop of the allergen or control solution was administered to the lower conjunctival fornix of one eye. Subjective and objective symptoms were recorded by the patient and the operator at 5, 10, 15, 20, and 30 minutes after challenge on a visual continuous analogue scale between 0 (no symptoms) to 100% (maximum of symptoms tolerable). Subjective symptoms were recorded by the patient, and consisted of itching, burning, lachrymation, and photophobia. Objective symptoms, recorded by the operator, were erythema, edema, vasal conjunctival injection, and lachrymation. In some cases, macro photographic pictures with a reproduction ratio of 1:1 were taken at 20', to validate the objective readings. When the reaction failed to reach after 20 minutes a score of 50% or greater in at least 2 of the parameters under study, the test was repeated in the controlateral eye using the next, more concentrated, allergen concentration. All the patients responded to the first or the second allergen dose. This provoking dose was then used for the subsequent experimental conjunctival challenges.

Study design

After the conjunctival sensitivity was established in the preliminary test, each patient performed two conjunctival challenges at a weekly interval, performed after pre-treatment with 4 drops of furosemide 10 mg/ml (®Lasix, Hoechst) or placebo, according to a randomized, double blind protocol. Two drops of the treatment were administered on each eye five minutes before the test, and 2 immediately before challenge with a single provocative dose of allergen. The test was then performed as described for the preliminary test.

STATISTICAL ANALYSIS

Paired analysis of data obtained with the analogue scale was performed using standard nonparametric techniques, despite they were recorded on a continuous scale, as no assumptions could be done on linearity (Maatthews DE, Farewell WT. Using and understanding medical statistics, $2^{nd}$ edition. Karger, Basel, 1988). Analysis of variance was used for multiple comparisons. A p value of 0.05 for a two-tail test was considered significant.

RESULTS

After treatment with placebo, sensitive subjects responded to ocular challenge with itching, burning, vascular injection, erythema and lachrymation, while sensation of ocular burning, photophobia, and edema were more irregularly distributed. Two patients also reported sneeze and rhinorrhea, probably due to leakage of allergen to the nose via the naso-lachrymal duct. A considerable degree of variability was observed in the intensity and tuning of the subjective and the objective parameters of the response to conjunctival challenge in the various subjects, as indicated by FIGS. 1 to 10, where the scores obtained in each subject during the placebo and furosemide challenge are reported. Descriptive statistical parameters of the subjective scores are reported in table II, and of objective scores in table III. All the signs and symptoms were usually present 5 minutes after challenge, and did not vary significantly at the different time points up to 20 minutes, although subjective symptoms appeared to be more evident at the early time points while objective signs seemed to increase more gradually during challenge. By contrast, subjective scores of lachrymation appeared to raise later than objective scores of the same symptom, reflecting the different timing between when tears begin to accumulate on the palpebral rim (subjective sensation) and when they are actually discharged (objective evaluation). Despite this fact, a good correlation was found between subjective and objective scores of lachrymation in the same subject (Spearman r being 0.79, p smaller than 0.001), indicating the general dependability of the evaluation.

After treatment with furosemide, most sign and symptom scores appeared decreased compared to placebo, although the uneven distribution of the different symptoms and timing among the subjects greatly limits the statistical evaluation of the differences, because of the presence of several ties in each group. Despite this fact, the Wilcoxon rank test indicated a significant decrease of the scores relative to pruritus and lachrymation at 15 and 20 minutes.

To obviate the problem of the uneven distribution of symptoms, the mean symptom score was evaluated as the average of all the objective or subjective scores at each time point (Table IV, FIGS. 11 and 12). The analysis of variance of total subjective scores indicated a significant difference between the two treatments regardless of time (p smaller than 0.02). Using Wilcoxon test, a significant decrease of the total subjective score was observed after furosemide at 10, 15 and 20 minutes from challenge, as well as for the maximum value. By contrast, no significant differences were found at any time point between total objective scores after furosemide or placebo, despite the fact that analysis of variance indicated a significant difference between treatments (p smaller than 0.01).

To individuate the main symptoms responsible for the protective effect of furosemide on the subjective symptom scores, avoiding the problems due to the uneven timing of symptoms in different subjects, the mean score was evaluated for each subject between 5 and 20 minutes from challenge, as the analysis of variance failed to reveal any significant difference of mean scores during this period (FIG. 13). A significant difference was found between the mean scores of itching and lachrymation after furosemide and placebo, while no significant differences ere found for all the other symptom and sign scores.

As most of the variability of the objective scores were due to a single patient (No.5), the analysis was repeated excluding this outlier from calculations. The Wilcoxon signed rank sum test then indicated a significant difference of both subjective (p greater than 0.02) and objective scores (p greater than 0.05). The effect on objective scores appeared to be mostly related to an effect on erythema and vascular injection at 15 and 20 minutes after challenge (p smaller than 0.05).

Finally, to validate objective sign scores, picture slides taken during challenge with the objective scores recorded at the same time point were examined. A total of 48 pictures, relative to 24 different conjunctival challenges were examined by 3 independent readers, giving a single total score to each picture. Readings from the 3 readers resulted well correlated, and Spearman correlation coefficient in the 3 paired comparison varied between 0.83 to 0.90 (p smaller than $10^{-6}$). When the mean picture score was compared to the objective score recorded during the same test, a significant positive correlation was observed with the mean objective score (r is 0.636, p smaller than 0.001). Among the different objective parameters recorded during challenge, vascular injection was the one more strictly correlated with the picture readings (r is 0.639, p smaller than 0.001). A complete set of pictures comprising both the placebo and furosemide test was available in 8 cases. No significant differences were found in the picture scores between the two treatments in this group.

DISCUSSION

The conjunctival test has been widely used for the diagnosis of allergy over the years, and it has been found suitable for clinical testing (Moller C, Bjiorksten B, Nilsson G, Dreborg S. The precision of conjuntival provocation test. Allergy 1984, 39:37-41) and for the study of the pathogenetic mechanisms of the allergic inflammation in the eye (Bonini S, Bonini S, Vecchione A et al. Inflammatory changes in conjunctival scrapings after allergen provocation in humans. J Allergy Clin Immunol 1988, 82: 462-9; Bonini S, Bonini S, Berruto A, Tomassini M, Carlesimo S, Bucci MG, Balsano F. Conjunctival provocation test as a model for the study of allergy and inflammation in humans. Int Arch Allergy Appll Immunol 1989 88:144-148). According to the instant invention, we used the specific conjunctival test to evaluate the potential therapeutical value of local treatment with furosemide on allergic conjunctivitis. The evaluation of the test proved to be relatively reproducible, despite the lack of instrumental parameters, although the considerable between subject variability creates some difficulties in the comparison of homogeneous groups. Local treatment with furosemide significantly reduced both objective and subjective scores compared to placebo, although the effect appeared more evident on some of the latter rather than on objective signs of inflammation, probably reflecting the greater variability of these parameters. The data according to the invention indicate that furosemide does have a protective effect on the specific conjunctival allergen challenge.

Taken together, the data indicate that local treatment with furosemide is very well tolerated and significantly reduces the conjunctival reaction induced by specific allergen challenge in subjects with seasonal allergic conjunctivitis. These results indicate that furosemide is of potential value for the treatment of the allergic diseases of the eye.

'TABLE I

Clinical characteristics of the patients investigated

| N | Sex | Age | Symptoms | Allergen[1] used | Dose (AUR) | Other skin Reactions[1] |
|---|-----|-----|----------|------------------|------------|-------------------------|
| 1 | F | 45 | Seasonal rhino-conjunctivitis | Pa | 32 | |
| 2 | M | 18 | Seasonal rhino-conjunctivitis | Gr | 32 | |
| 3 | F | 23 | Seasonal rhino-conjunctivitis | Pa | 100 | Gr DP |
| 4 | M | 17 | Seasonal rhino-conjunctivitis | Gr | 100 | |
| 5 | M | 37 | Seasonal rhino-conjunctivitis | Gr | 320 | Pa, Ol, Cy |
| 6 | M | 27 | Seasonal rhino-conjunctivitis | Gr | 100 | |
| 7 | M | 49 | Seasonal rhino-conjunctivitis and asthma | Gr | 32 | Ol, Comp |
| 8 | M | 18 | Seasonal rhino-conjunctivitis | Gr | 10 | |
| 9 | F | 12 | Seasonal rhino-conjunctivitis and asthma | Gr | 100 | |
| 10 | M | 22 | Seasonal rhino-conjunctivitis | Gr | 32 | Pa |

[1] Gr: grass pollen. Pa: *Parietaria officinalis*. Ol: Olive tree, Cy: cypress, Comp: compositae. DP: *Dermatophagoides pteronissimus*.

TABLE II

Effect of Furosemide on subjective scores after allergen challenge

| | Placebo | | Furosemide | |
|------|--------|------------|--------|------------|
| TIME | Median | Mean ± SE | Median | Mean ± SE |
| ITCHING | | | | |
| 0 | 0.0 | 0.0 ± 0.0 | 0.0 | 0.00 ± 0.0 |
| 5' | 14.0 | 27.80 ± 9.05 | 14.0 | 19.50 ± 5.26 |
| 10' | 11.0 | 18.50 ± 5.69 | 7.0 | 12.00 ± 4.94 |
| 15' | 10.0 | 14.70 ± 4.65 | 7.0 | 10.10 ± 3.48 |
| 20' | 12.0 | 15.60 ± 5.15 | 3.0 | 8.20 ± 3.95 |
| Mean[a] | 11.0 | 15.40 ± 4.17 | 6.0 | 10.00 ± 3.12 |
| Max[b] | 20.0 | 30.50 ± 9.29 | 14.0 | 22.10 ± 5.53 |

TABLE II-continued

Effect of Furosemide on subjective scores after allergen challenge

| TIME | Placebo | | Furosemide | |
|------|---------|----------------|------------|----------------|
|      | Median  | Mean ± SE      | Median     | Mean ± SE      |
| BURNING | | | | |
| 0    | 0.0     | 0.0 ± 0.0      | 0.0        | 0.00 ± 0.0     |
| 5'   | 8.0     | 18.50 ± 7.37   | 1.5        | 5.80 ± 2.61    |
| 10'  | 2.5     | 11.80 ± 4.67   | 0.0        | 7.90 ± 4.26    |
| 15'  | 1.5     | 12.60 ± 5.60   | 0.0        | 9.40 ± 6.24    |
| 20'  | 1.0     | 12.90 ± 6.20   | 0.0        | 10.90 ± 7.38   |
| Mean | 6.0     | 11.10 ± 4.29   | 1.0        | 6.70 ± 3.60    |
| Max  | 12.0    | 22.70 ± 8.00   | 6.0        | 15.20 ± 7.04   |
| PHOTOPHOBIA | | | | |
| 0    | 0.0     | 0.0 ± 0.0      | 0.0        | 0.00 ± 0.0     |
| 5'   | 0.0     | 10.10 ± 5.96   | 0.0        | 4.10 ± 2.16    |
| 10'  | 1.0     | 6.00 ± 3.44    | 0.0        | 4.80 ± 3.08    |
| 15'  | 1.0     | 7.20 ± 4.54    | 0.0        | 3.10 ± 2.19    |
| 20   | 1.0     | 6.60 ± 5.08    | 0.0        | 3.30 ± 2.89    |
| Mean | 1.5     | 6.00 ± 3.42    | .5         | 3.20 ± 1.89    |
| Max  | 4.5     | 13.30 ± 6.29   | 1.5        | 6.40 ± 3.25    |
| LACHRYMATION | | | | |
| 0    | 0.0     | 0.0 ± 0.0      | 0.0        | 0.00 ± 0.0     |
| 5'   | 6.0     | 10.20 ± 3.84   | 2.5        | 6.80 ± 2.60    |
| 10'  | 7.5     | 12.50 ± 4.78   | 1.0        | 9.10 ± 3.72    |
| 15'  | 7.5     | 16.30 ± 7.49   | 0.0        | 10.20 ± 6.59   |
| 20'  | 4.5     | 18.60 ± 8.96   | 0.0        | 11.40 ± 7.72   |
| Mean | 4.5     | 11.40 ± 4.81   | 1.0        | 7.40 ± 3.59    |
| Max  | 13.5    | 21.70 ± 8.43   | 3.5        | 16.40 ± 7.48   |

Notes for table II:
[a] Mean value of the scores recorded between 5 and 20 minutes after challenge.
[b] Maximum value of the scores recorded between 5 and 20 minutes after challenge.

TABLE III

Effect of Furosemide on objective scores after allergen challenge

| TIME | Placebo | | Furosemide | |
|------|---------|----------------|------------|----------------|
|      | Median  | Mean ± SE      | Median     | Mean ± SE      |
| ERYTHEMA | | | | |
| 0    | 0.0     | 0.0 ± 0.0      | 0.0        | 0.00 ± 0.0     |
| 5'   | 17.5    | 19.50 ± 4.92   | 10.0       | 13.20 ± 3.24   |
| 10'  | 18.5    | 22.80 ± 5.31   | 11.0       | 14.00 ± 3.09   |
| 15'  | 20.5    | 24.60 ± 5.71   | 10.0       | 18.60 ± 6.76   |
| 20'  | 27.5    | 28.30 ± 5.93   | 8.5        | 17.80 ± 6.46   |
| Mean | 15.5    | 18.90 ± 4.06   | 8.5        | 12.60 ± 3.32   |
| Max  | 27.5    | 31.20 ± 6.18   | 19.0       | 25.20 ± 6.33   |
| EDEMA | | | | |
| 0    | 0.0     | 0.0 ± 0.0      | 0.0        | 0.00 ± 0.0     |
| 5'   | 2.0     | 5.70 ± 2.34    | 1.0        | 2.50 ± .96     |
| 10'  | 5.0     | 7.50 ± 2.13    | 1.5        | 3.90 ± 1.73    |
| 15'  | 4.0     | 6.70 ± 2.39    | 1.0        | 7.10 ± 3.67    |
| 20'  | 3.5     | 5.80 ± 2.04    | 0.0        | 8.30 ± 5.78    |
| Mean | 3.0     | 5.20 ± 1.71    | 2.0        | 4.40 ± 2.15    |
| Max  | 5.5     | 8.40 ± 2.18    | 5.0        | 10.6 ± 5.71    |
| VASCULAR INJECTION | | | | |
| 0    | 0.0     | 0.0 ± 0.0      | 0.0        | 0.00 ± 0.0     |
| 5'   | 26.5    | 27.80 ± 4.58   | 18.0       | 21.80 ± 2.98   |
| 10'  | 30.5    | 31.70 ± 3.61   | 21.0       | 22.60 ± 4.46   |
| 15'  | 35.0    | 32.50 ± 5.19   | 18.5       | 22.80 ± 5.97   |
| 20'  | 35.5    | 35.50 ± 5.32   | 21.5       | 23.60 ± 6.77   |
| Mean | 27.0    | 25.60 ± 3.17   | 14.5       | 18.20 ± 3.54   |
| Max  | 38.0    | 40.70 ± 5.17   | 31.0       | 31.70 ± 5.17   |
| LACHRYMATION | | | | |
| 0    | 0.0     | 0.0 ± 0.0      | 0.0        | 0.00 ± 0.0     |
| 5'   | 11.5    | 10.00 ± 2.42   | 3.0        | 8.20 ± 4.11    |
| 10'  | 9.0     | 11.60 ± 3.15   | 2.0        | 7.20 ± 4.83    |
| 15'  | 3.0     | 10.20 ± 4.36   | .5         | 9.20 ± 6.68    |
| 20'  | 5.5     | 15.00 ± 5.98   | 2.0        | 7.00 ± 4.22    |

TABLE III-continued

Effect of Furosemide on objective scores after allergen challenge

| TIME | Placebo | | Furosemide | |
|------|---------|----------------|------------|----------------|
|      | Median  | Mean ± SE      | Median     | Mean ± SE      |
| Mean | 7.0     | 9.30 ± 2.74    | 1.5        | 6.30 ± 3.86    |
| Max  | 14.0    | 19.50 ± 5.69   | 6.5        | 12.40 ± 6.37   |

TABLE IV

Effect of Furosemide on total mean scores after allergen challenge

| TIME | Placebo | | Furosemide | |
|------|---------|----------------|------------|----------------|
|      | Median  | Mean ± SE      | Median     | Mean ± SE      |
| TOTAL SUBJECTIVE | | | | |
| 0    | 0.0     | 0.0 ± 0.0      | 0.0        | 0.00 ± 0.0     |
| 5'   | 12.0    | 16.70 ± 5.40   | 7.0        | 8.90 ± 1.89    |
| 10'  | 9.0     | 12.20 ± 3.62   | 6.5        | 8.50 ± 3.20    |
| 15'  | 7.0     | 12.80 ± 4.52   | 2.0        | 8.30 ± 3.62    |
| 20'  | 5.5     | 13.50 ± 5.39   | .5         | 8.40 ± 4.90    |
| Mean | 7.5     | 11.00 ± 3.38   | 3.0        | 6.70 ± 2.47    |
| Max  | 12.5    | 20.90 ± 5.96   | 8.0        | 13.60 ± 4.29   |
| TOTAL OBJECTIVE SCORE | | | | |
| 0    | 0.0     | 0.0 ± 0.0      | 0.0        | 0.00 ± 0.0     |
| 5'   | 13.5    | 15.80 ± 2.88   | 9.0        | 11.40 ± 2.09   |
| 10'  | 16.5    | 18.40 ± 2.88   | 8.5        | 12.00 ± 3.01   |
| 15'  | 20.0    | 18.50 ± 3.58   | 6.5        | 14.40 ± 5.35   |
| 20'  | 19.5    | 21.20 ± 4.08   | 8.5        | 14.20 ± 5.38   |
| Mean | 14.0    | 14.80 ± 2.58   | 7.0        | 10.30 ± 2.90   |
| Max  | 20.0    | 22.40 ± 4.09   | 13.0       | 18.70 ± 4.91   |

Figure 1:
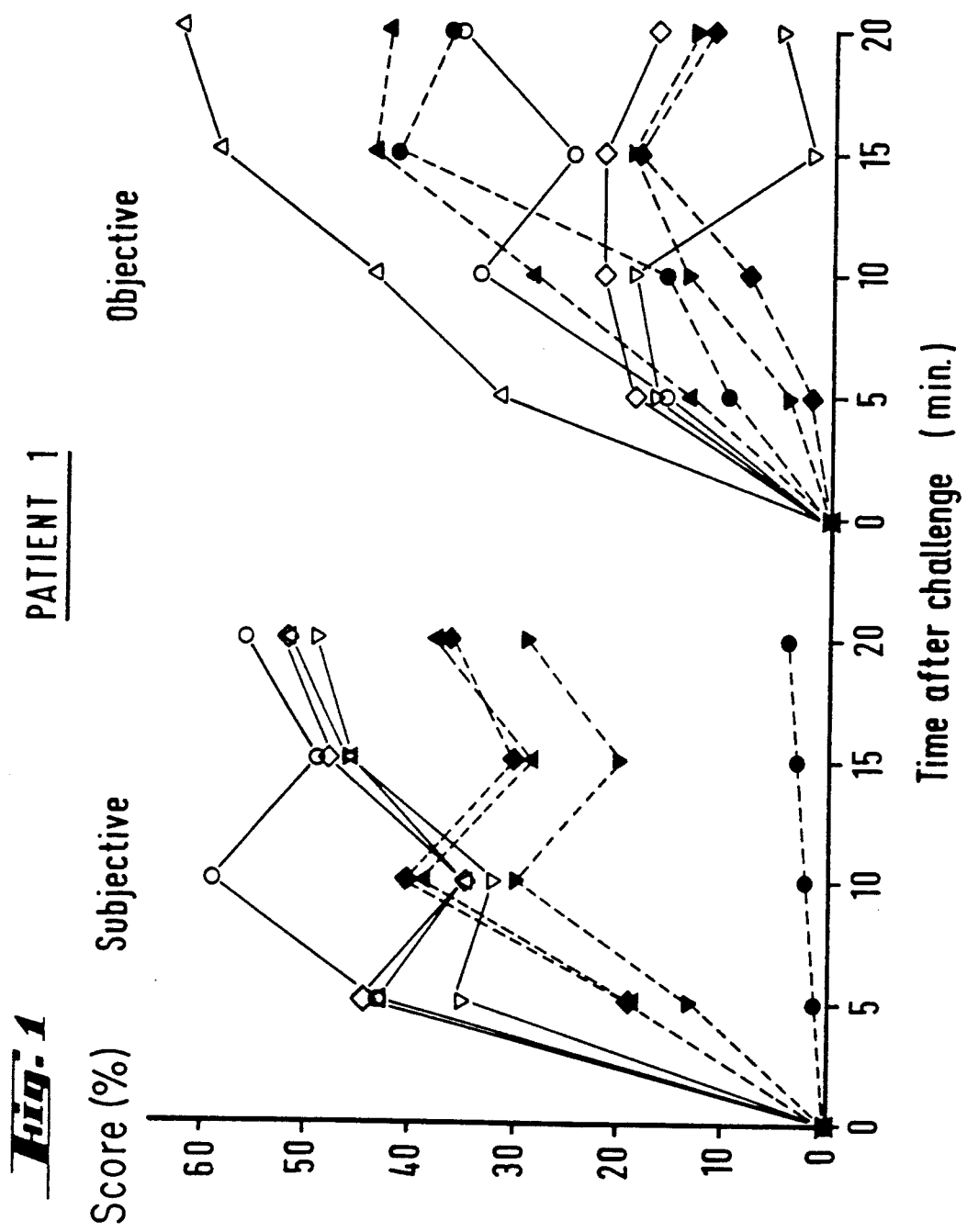
FIGS. 1-10. Individual values of subjective (left) and objective (right) symptom scores recorded during specific allergen challenge after treatment with placebo (open symbols, continuous lines).or furosemide (filled symbols, dotted lines) for each patient No. 1-No. 10. Subjective symptoms : hitching (circle), burning (diamond), photophobia (triangle), lachrymation (inverted triangle). Objective signs: erythema (circle), edema (diamond), vascular injection (triangle), lachrymation (inverted triangle); the score is plotted against the time after challenging.
Figure 2:
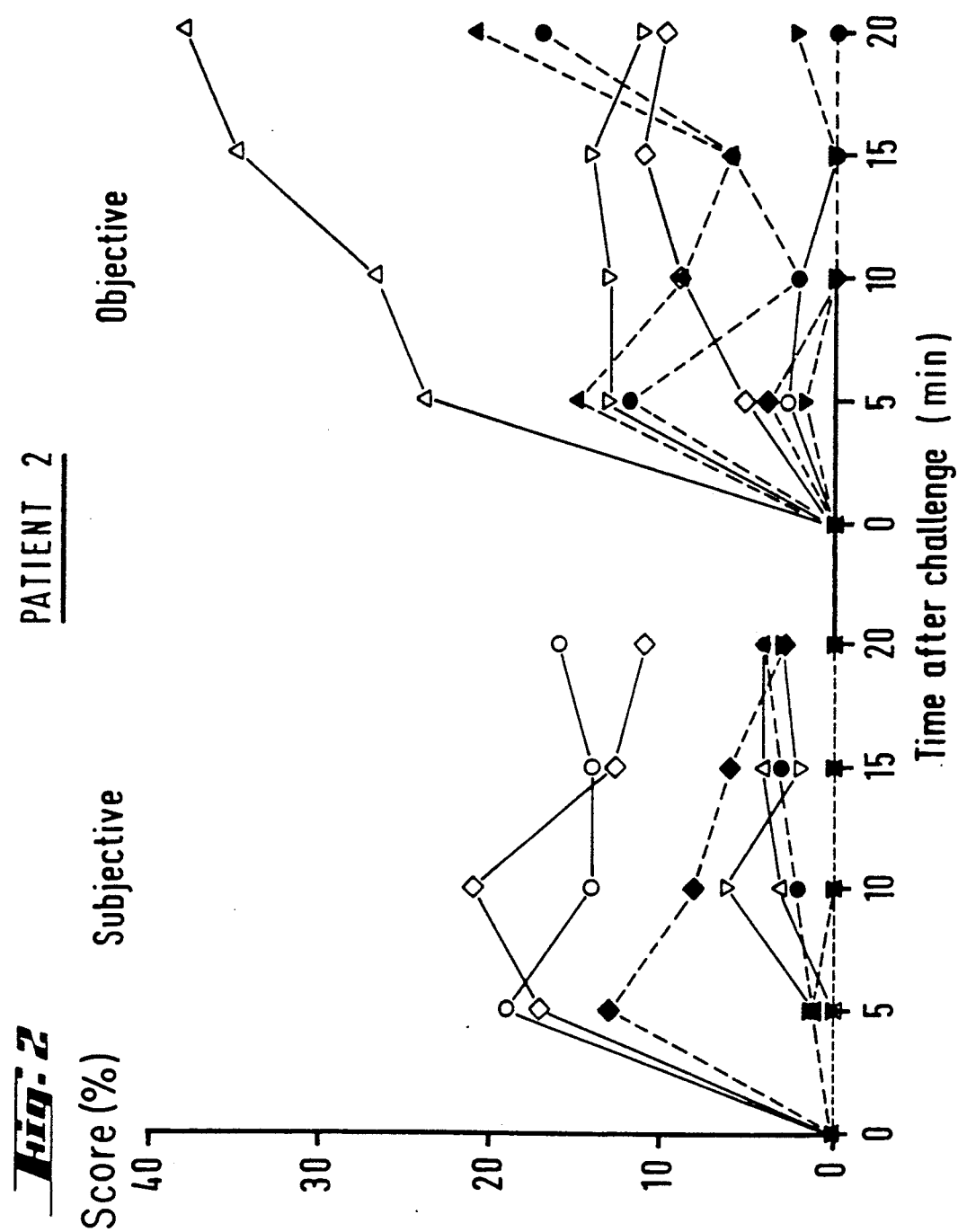
Figure 3:
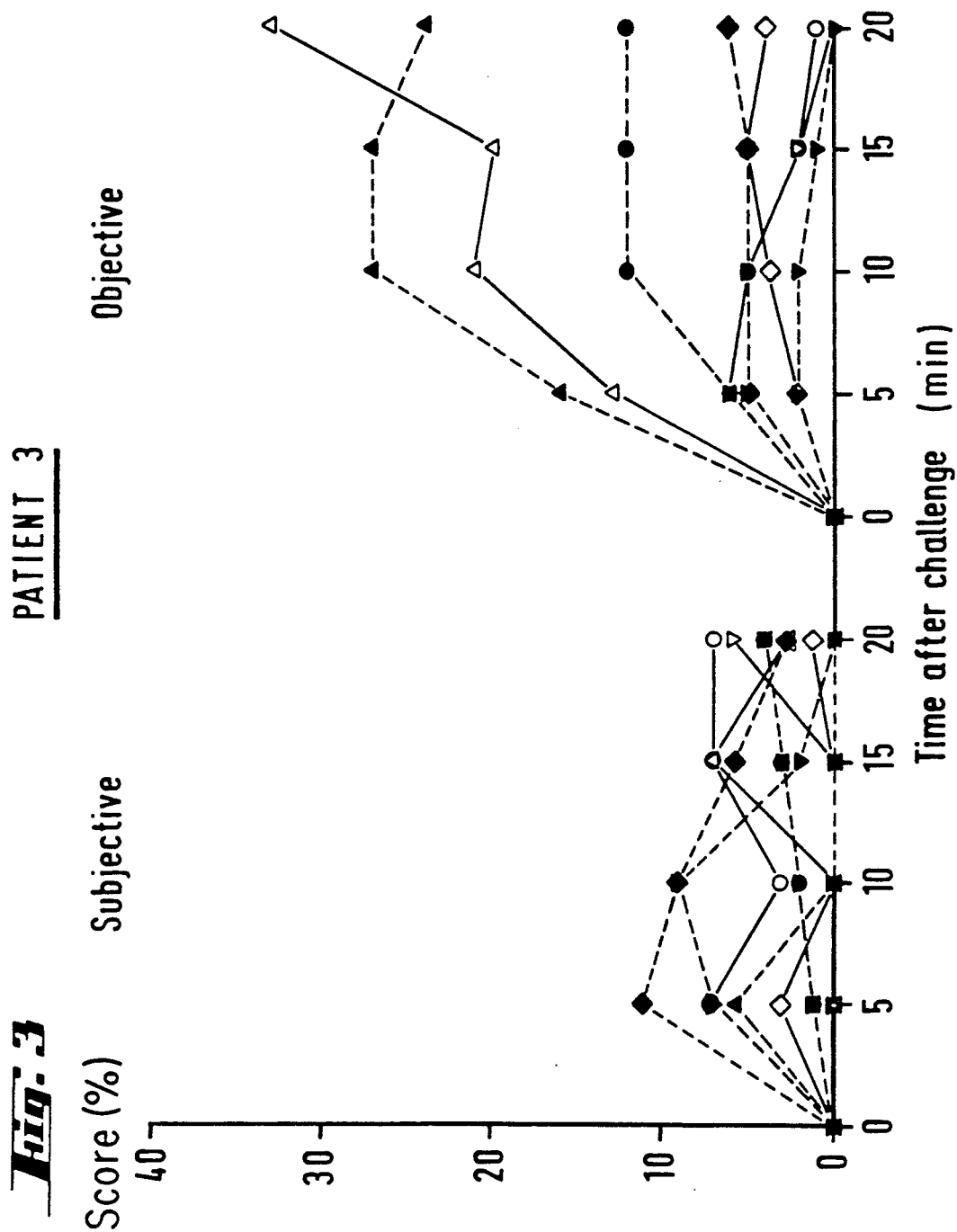
Figure 4:
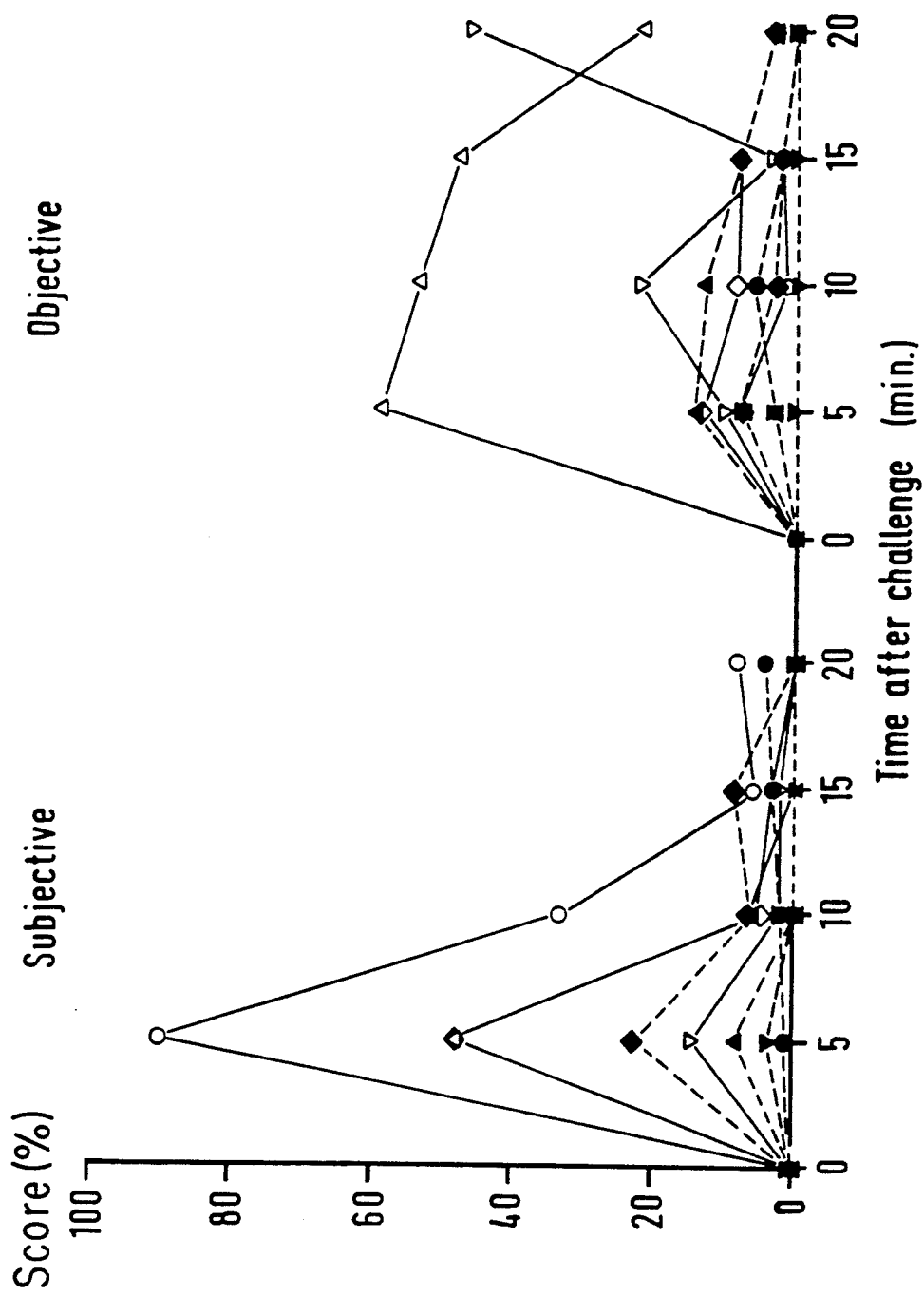
Figure 5:
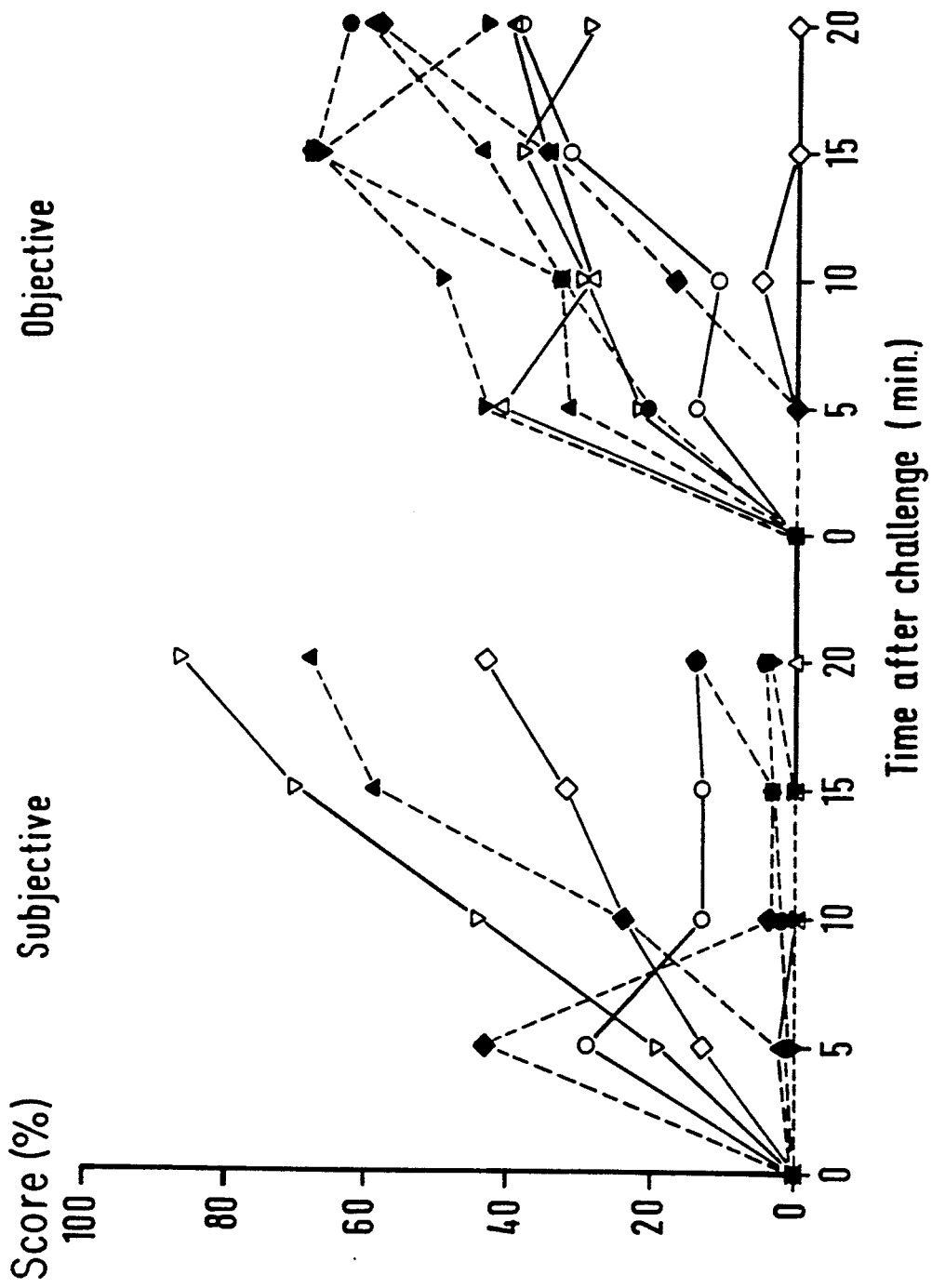
Figure 6:
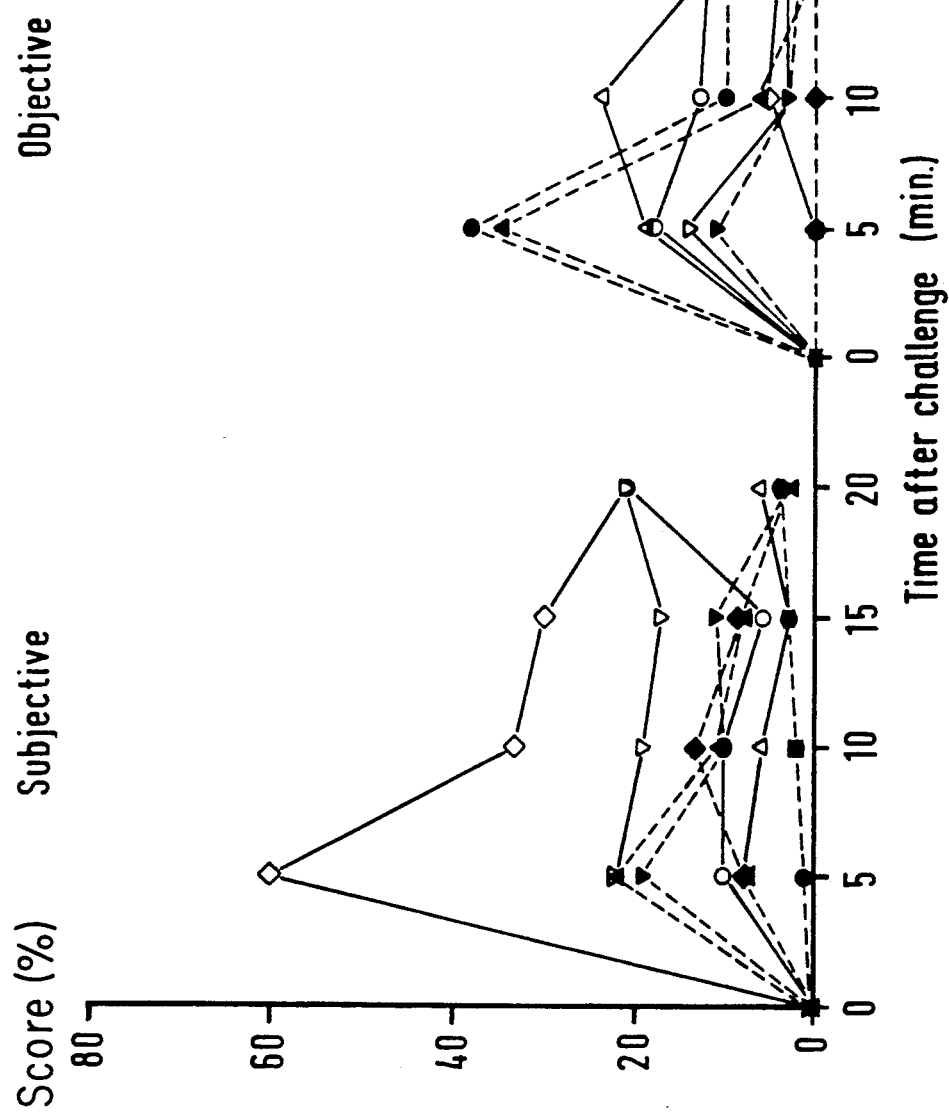
Figure 7:
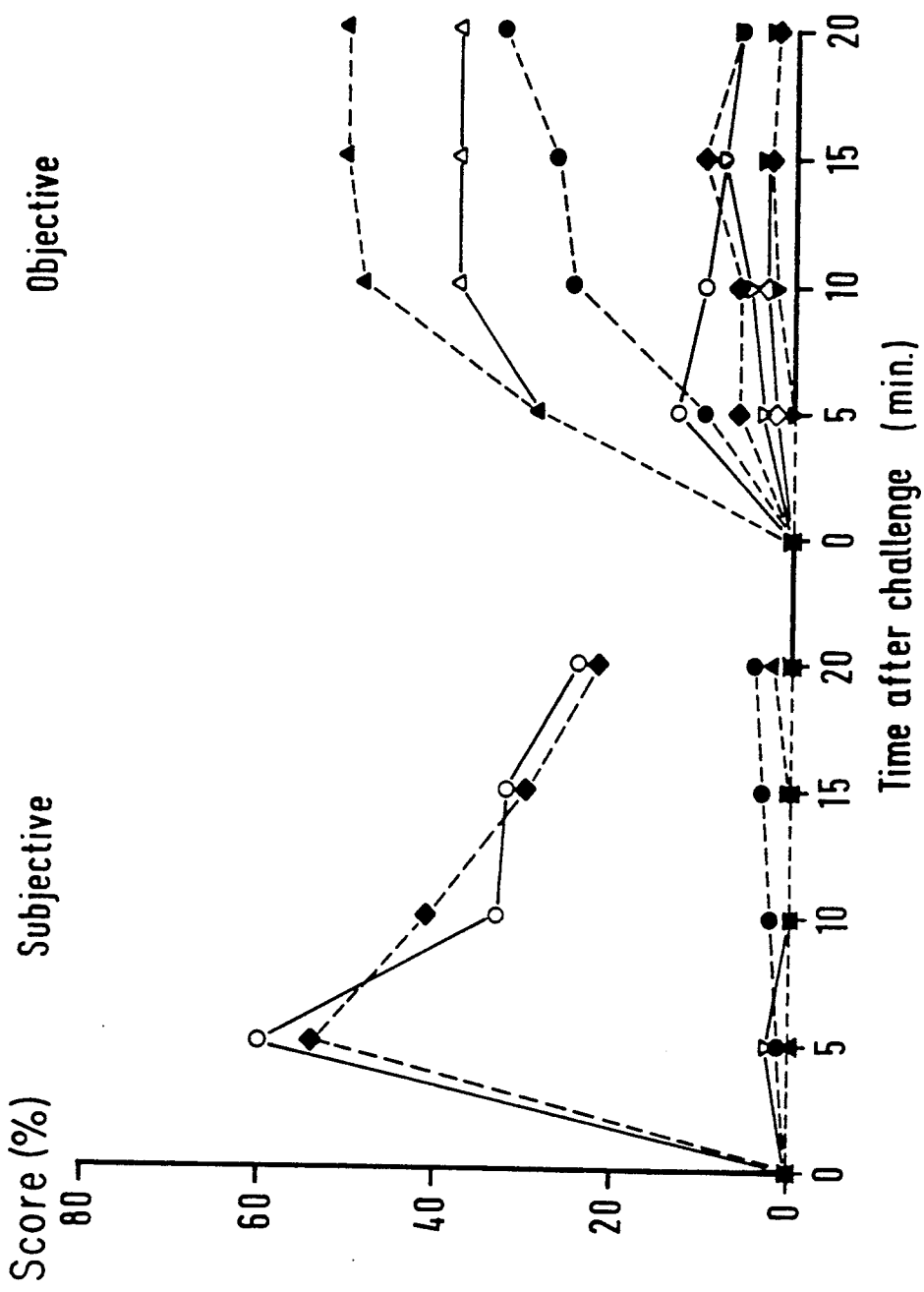
Figure 8:
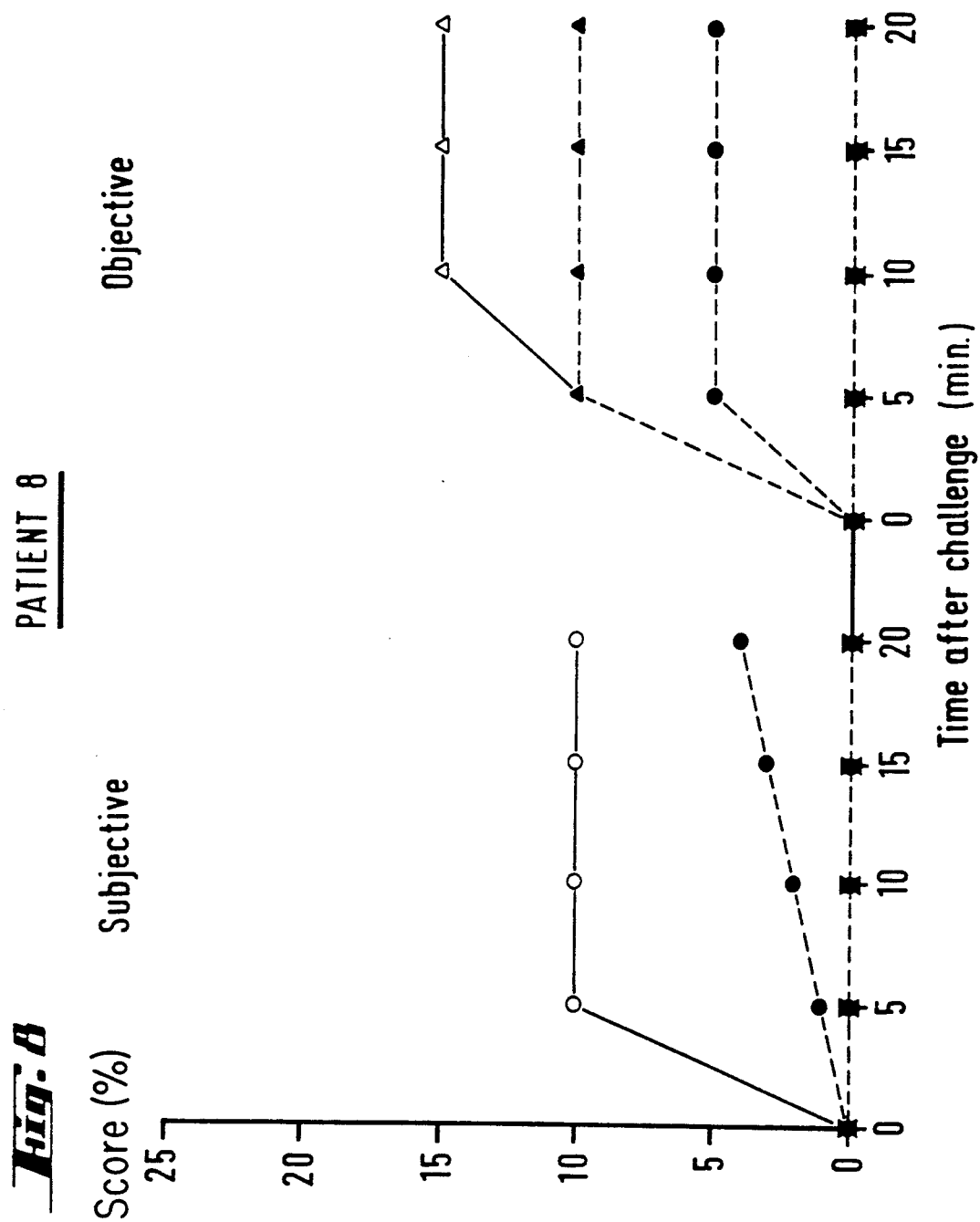
Figure 9:
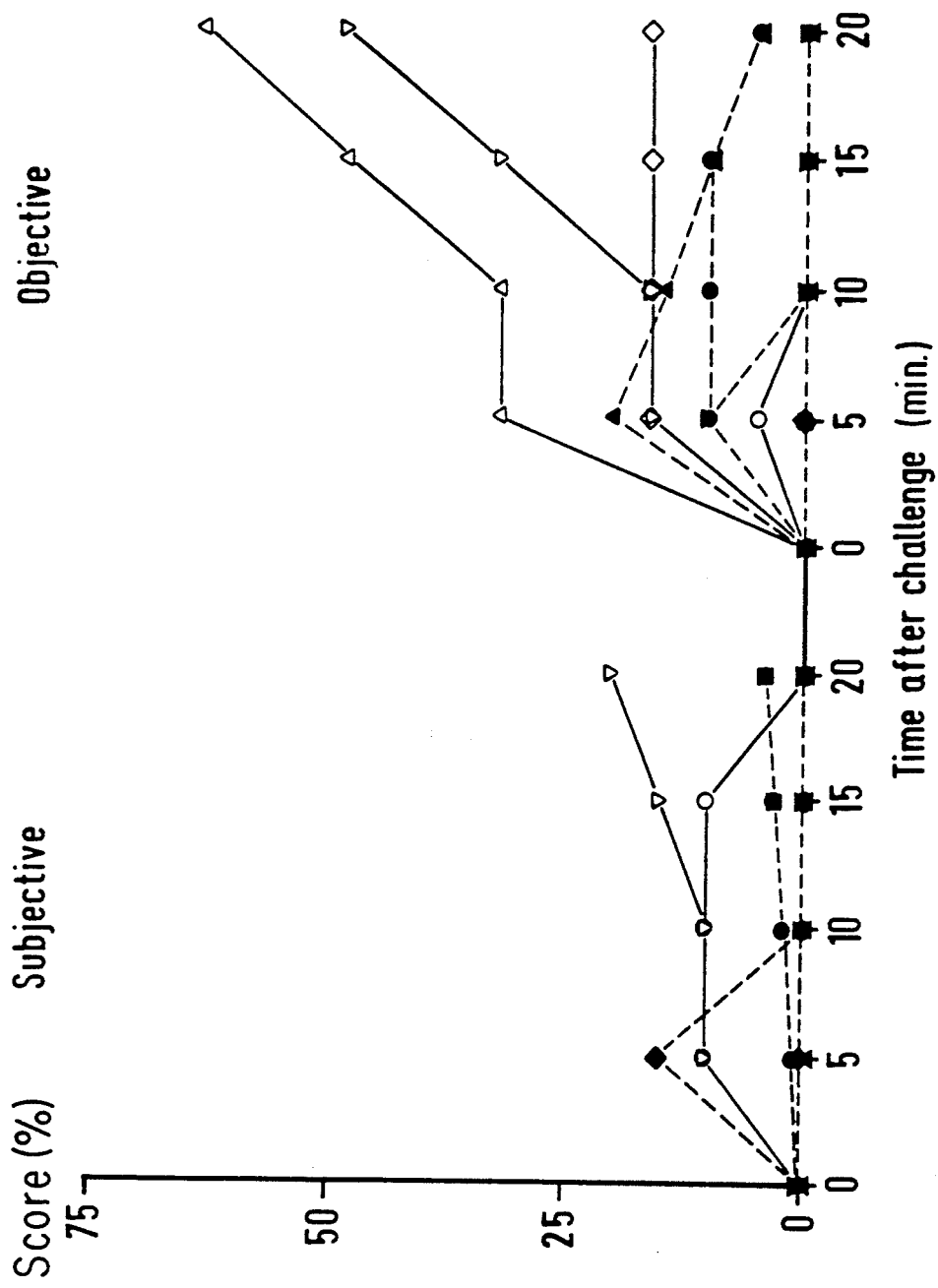
Figure 10:
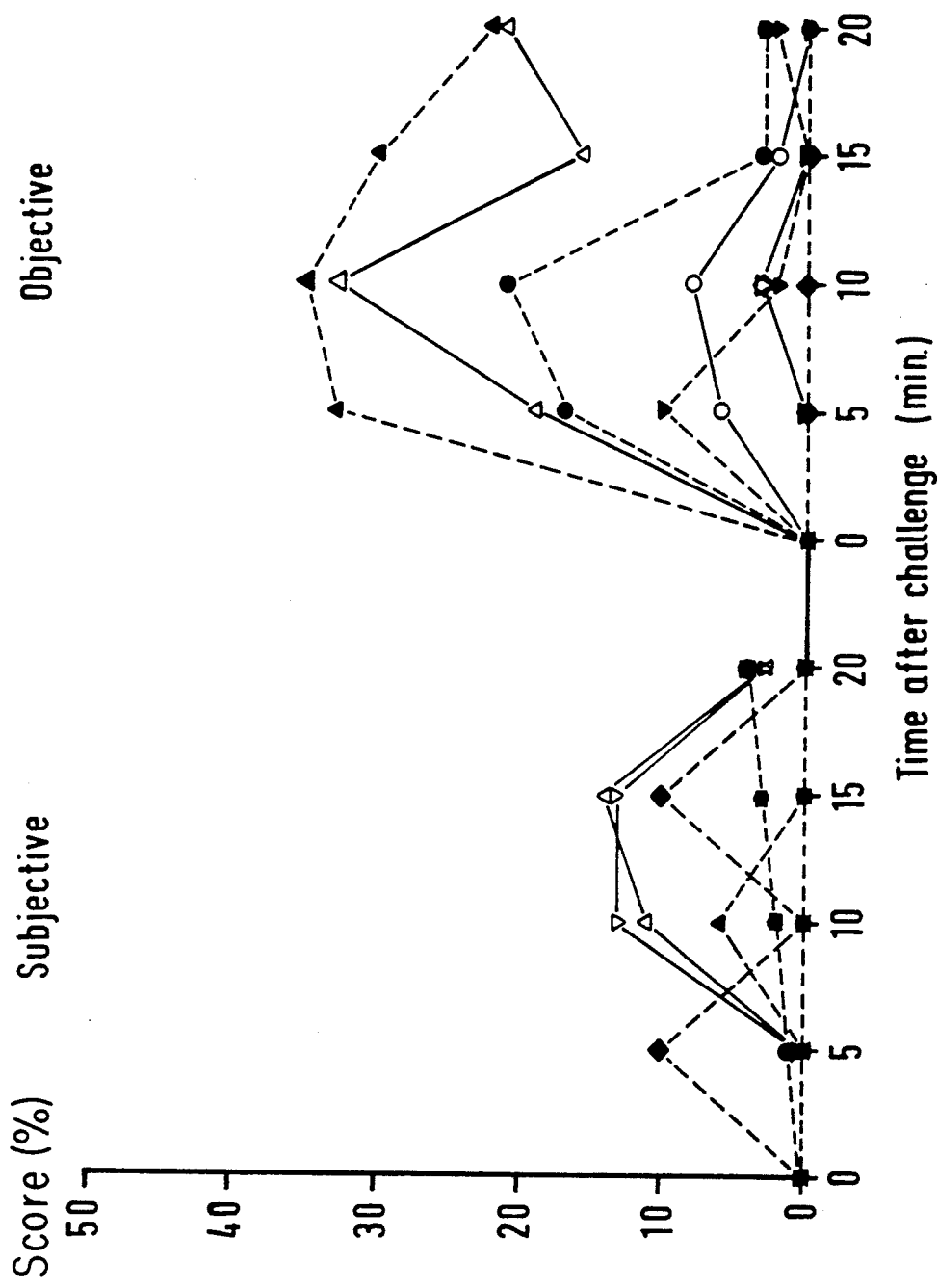
Figure 11:
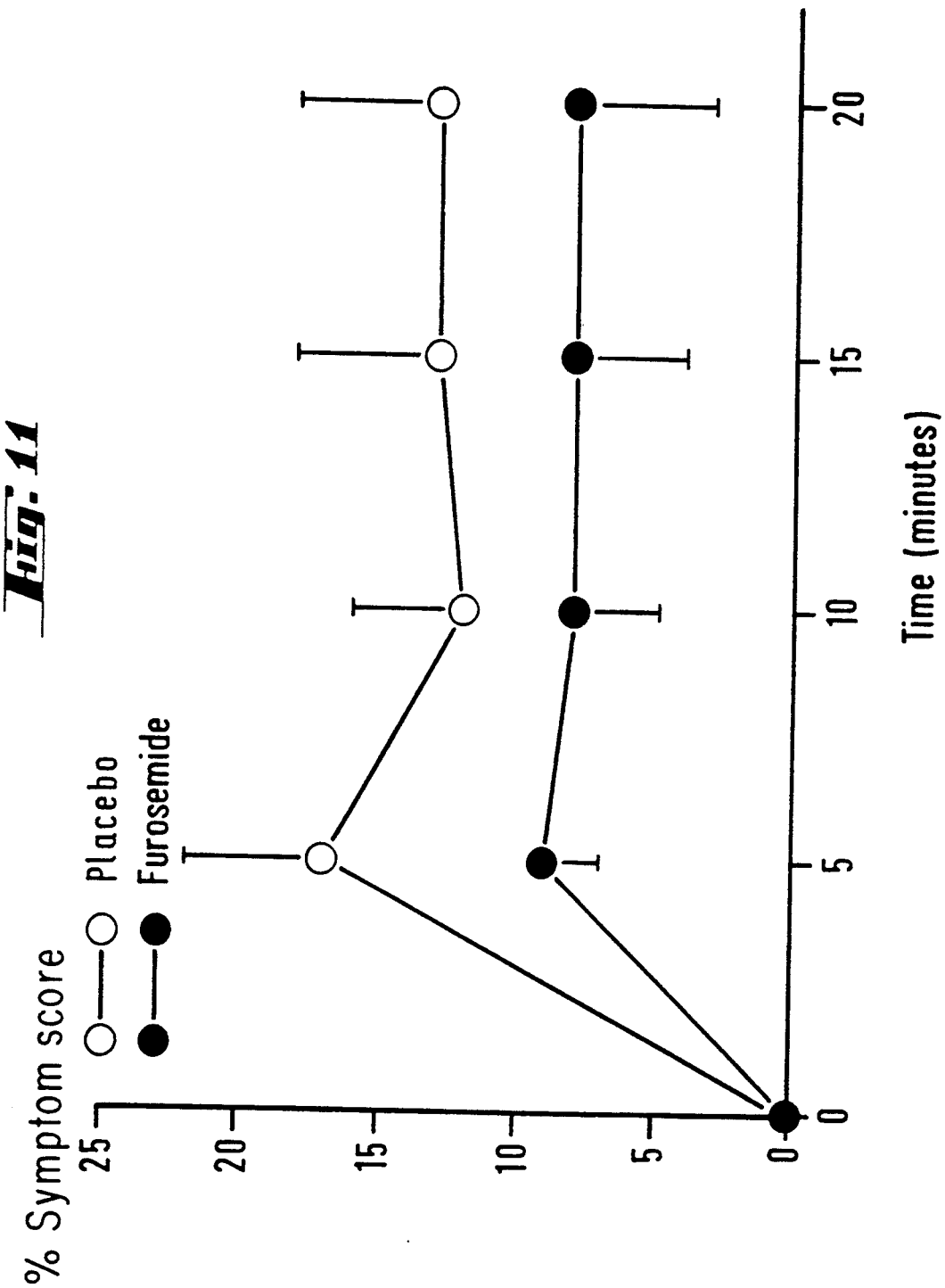
FIG. 11. Mean value and SE of total subjective scores recorded during challenge after treatment with placebo (open symbols I or furosemide (filled symbols I).Analysis of variance showed a significant difference between treatments (p smaller than 0.02) but no significant variations over time between 5 and 20 minutes.
Figure 12:
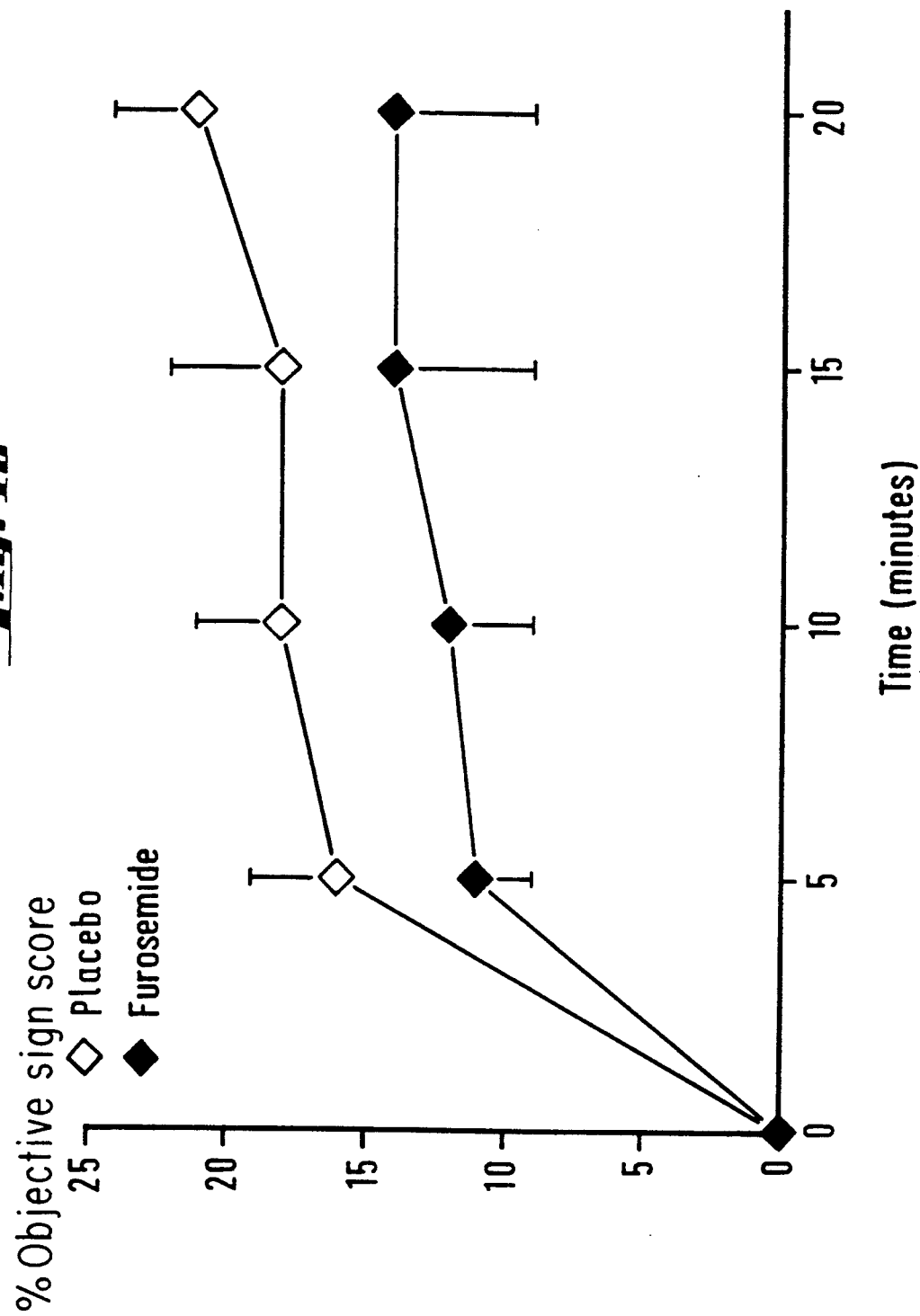
FIG. 12. Mean value and SE of total objective scores recorded during challenge after treatment with placebo (open symbols) or furosemide (filled symbols I). Analysis of variance showed a significant difference between treatments (p smaller than 0.01) but no significant variations over time between 5 and 20 minutes.
Figure 13:
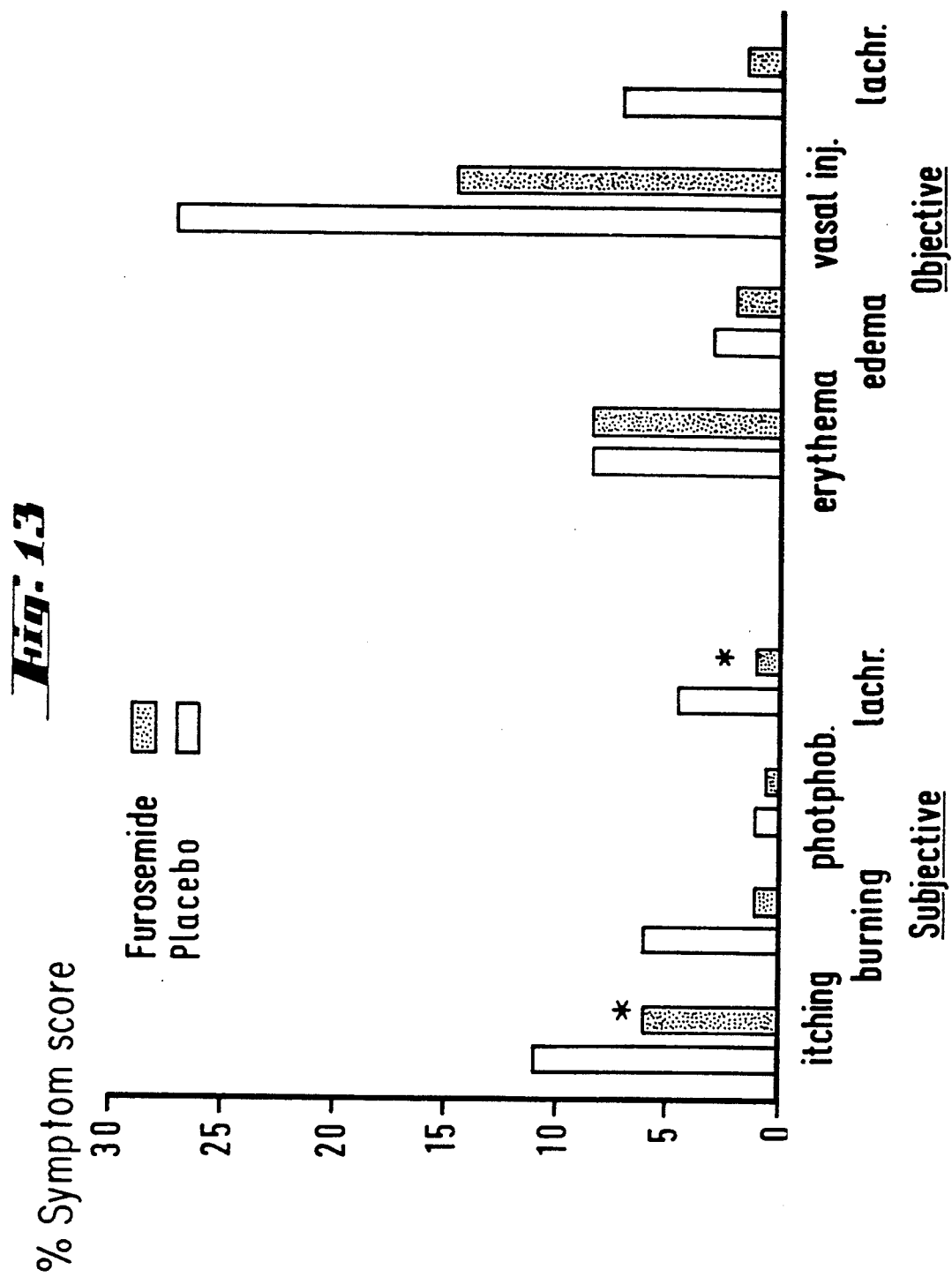
FIG. 13. Median value of the mean score recorded between 5 and 20 minutes after challenge for each subjective and objective parameter, after treatment with placebo (open bars) or furosemide (filled). *) p smaller than 0.05, Wilcoxon rank sum test.

I claim:

1. A method of treating or preventing allergic conjunctivitis which consists in administering an effective amount of furosemide to the conjunctive fornix of the eye.

* * * * *